United States Patent
Netravali et al.

(10) Patent No.: US 10,405,910 B2
(45) Date of Patent: Sep. 10, 2019

(54) SYSTEMS AND PROCESSES FOR REVISION TOTAL JOINT ARTHROPLASTY

(71) Applicant: CUREXO TECHNOLOGY CORPORATION, Fremont, CA (US)

(72) Inventors: Nathan A Netravali, Palo Alto, CA (US); In K Mun, Nanuet, NY (US)

(73) Assignee: THINK SURGICAL, INC., Fremont, CA (US)

(*) Notice: Subject to any disclaimer, the term of this patent is extended or adjusted under 35 U.S.C. 154(b) by 1018 days.

(21) Appl. No.: 14/777,493

(22) PCT Filed: Mar. 17, 2014

(86) PCT No.: PCT/US2014/030384
§ 371 (c)(1),
(2) Date: Sep. 15, 2015

(87) PCT Pub. No.: WO2014/145591
PCT Pub. Date: Sep. 18, 2014

(65) Prior Publication Data
US 2016/0030126 A1 Feb. 4, 2016

Related U.S. Application Data

(60) Provisional application No. 61/788,656, filed on Mar. 15, 2013.

(51) Int. Cl.
*A61B 34/10* (2016.01)
*A61B 17/92* (2006.01)
(Continued)

(52) U.S. Cl.
CPC .............. *A61B 17/92* (2013.01); *A61B 34/10* (2016.02); *A61F 2/4657* (2013.01); *A61B 34/30* (2016.02);
(Continued)

(58) Field of Classification Search
CPC ..... A61B 17/92; A61B 17/8847; A61B 34/10; A61F 2/30942; A61F 2/4607
(Continued)

(56) References Cited

U.S. PATENT DOCUMENTS 5,086,401 A 2/1992 Glassman et al.
5,192,283 A 3/1993 Ling et al.
(Continued)

FOREIGN PATENT DOCUMENTS

WO 2014045119 A2 3/2014

OTHER PUBLICATIONS

Link, Thomas M.; Beming, Wilfried; Scherf, Steffi; Joosten, Uwe; Joist, Alexander; Engelke, Klaus; Daldrup-Link, Heike E. "CT of Metal Implants: Reduction of Artifacts Using an Extended CT Scale Technique"; Journal of Computer Assisted Tomography; Issue: vol. 24(1), Jan./Feb. 2000, pp. 165-172; © 2000 Lippincott Williams & Wilkins, Inc.
(Continued)

*Primary Examiner* — Si Mung Ku
(74) *Attorney, Agent, or Firm* — Avery N. Goldstein; Blue Filament Law PLLC

(57) ABSTRACT

A process and system for performing orthopedic surgery with the use of computer systems and robotic assistance to remove bone, bone cement, and a bone prosthesis, typically a bone prosthesis used in hip replacement surgery, knee replacement surgery, and the like. The process for replacing one or more bone prostheses using a robotic system includes receiving image data comprising an image of each bone, including at least one prosthesis implanted within each bone; creating three-dimensional models of the prosthesis, and the bone; creating a plan for positioning new prostheses within the bone; determining the location and amount of bone and any non-bone material to be removed for the new prosthe-
(Continued)

ses; and removing the bone prosthesis from the bone. The inventive process may be used for the replacement of hip joints, shoulder joints, ankle joints, wrist joints, finger joints, toe joints, or other joints.

16 Claims, 2 Drawing Sheets

(51) Int. Cl.
*A61F 2/46* (2006.01)
*A61F 2/30* (2006.01)
*A61B 90/00* (2016.01)
*A61B 34/30* (2016.01)

(52) U.S. Cl.
CPC ... *A61B 2034/104* (2016.02); *A61B 2034/105* (2016.02); *A61B 2090/364* (2016.02); *A61B 2090/3762* (2016.02); *A61B 2090/3966* (2016.02); *A61B 2090/3975* (2016.02); *A61F 2002/3069* (2013.01); *A61F 2002/4631* (2013.01); *A61F 2002/4633* (2013.01); *A61F 2002/4663* (2013.01)

(58) Field of Classification Search
USPC ..................................... 606/99; 600/414–416
See application file for complete search history.

(56) References Cited

U.S. PATENT DOCUMENTS

| | | | |
|---|---|---|---|
| 5,299,288 A | 3/1994 | Glassman et al. | |
| 5,408,409 A | 4/1995 | Glassman et al. | |
| 5,769,092 A * | 6/1998 | Williamson, Jr. | A61B 17/8847 128/898 |
| 5,824,085 A * | 10/1998 | Sahay | A61F 2/30942 128/898 |
| 7,542,791 B2 * | 6/2009 | Mire | G16H 50/50 600/407 |
| 2013/0108979 A1 * | 5/2013 | Daon | A61B 5/064 433/29 |

OTHER PUBLICATIONS

Guerrero, Maria Eugenia; Jacobs, Reinhilde ; Loubele, Miet; Schutyser, Filip; Suetens, Paul; van Steenberghe, Daniel "State-of-the-art on cone beam CT imaging for preoperative planning of implant placement"; Clin Oral Invest (2006) 10: pp. 1-7; DOI 10.1007/s00784-005-0031-2; Review; Accepted: Dec. 13, 2005/Published online: Feb. 16, 2006; © Springer-Verlag 2006.

Besl, Paul J. et al. "A Method for Registration of 3-D Shapes", IEEE Transactions on Pattern Analysis and Machine Intelligence, vol. 14, No. 2, Feb. 1992, pp. 239-256.

Cohan, Steve "ROBODOC Achieves Pinless Registration", The Industrial Robot: An International Journal, 2001; vol. 28, No. 5; ProQuest, p. 381 386; current issue and full text at http://www.emerald-library.com/ft; research register at http://www.mcbup.com/research_registers.

Mittelstadt, Brent et al. "Development of a Surgical Robot for Cementless Total Hip Replacement", Robotica, vol. 11, Issue 6, Nov. 1993, pp. 553-560; http://journals.cambridge.org/abstract_S0263574700019408; http://journals.cambridge.org/ROB.

* cited by examiner

110: receive image data of a patient's bone with prosthesis implanted

120: create three-dimensional models of prosthesis, bone cement, bone

130: plan new prosthesis location within bone

140: determine location and amount of bone/bone cement to be removed

150: remove the prosthesis from the bone

160: registering the bone location in the robot's workspace

SYSTEMS AND PROCESSES FOR REVISION TOTAL JOINT ARTHROPLASTY

CROSS-REFERENCE TO RELATED APPLICATION

This application claims priority of U.S. Provisional Patent Application Ser. No. 61/788,656 filed Mar. 15, 2013, which is incorporated herein by reference.

FIELD OF THE INVENTION

The present invention relates generally to the field of computer-aided surgical systems, and more specifically to a new and useful system and method for performing computer-aided total joint arthroplasty.

BACKGROUND OF THE INVENTION

Total joint replacement (TJR) (also called primary total joint arthroplasty) is a surgical procedure in which the articulating surfaces of a joint are replaced with prosthetic components, or implants. It is a successful procedure, especially for hips, knees, shoulders, and ankles and allows people to restore functionality while greatly reducing pain associated with osteoarthritis.

Bone is a living tissue that is constantly changing through the resorption of matrix by osteoclasts and the deposition of new matrix by osteoblasts. Articular cartilage is an avascular tissue that is found on the surfaces of joints and serves to provide a smooth interface upon which bones can articulate with each other. Joint replacement arthroplasty is an orthopedic procedure in which the typically worn surface of the joint is replaced with a prosthetic component, or implant. Joint replacement arthroplasty typically requires the removal of the articulating cartilage surface of the joint including a varying amount of bone depending on the joint and the replacement implant being used. This cartilage and bone is then replaced with a synthetic, typically metal implant that is used to create a new joint surface.

The replacement implants used in joint replacement surgeries have a limited life expectancy and will often need to be replaced. Replacement of a joint replacement implant is called revision total joint replacement (RTJR) and involves removing the old implant(s) from the bone, removing any bone cement (polymethylmethacrylate or PMMA) used during the TJR, reshaping the bone to fit new revision implant(s), and placing the new revision implant(s) into the bone. RTJR is known to be a difficult and lengthy procedure because the surgeon typically has a limited amount of information about the location and amount of bone cement from the previous TJR. Removal of both the old implant and the bone cement is typically performed using a variety of hand tools including osteotomes, saws, punches, power saws, power burs, and ultrasonic instruments. However, these tools can be tedious to use especially when trying to remove bone cement from deeper cavities or small holes. Additionally, these tools present a risk of fracturing the bone when removing the implant or the bone cement. To increase visibility of the bone cement and bone-implant interface, holes or windows may be cut or drilled into the bone. However, this may weaken the bone and increase the risk of later fracture.

Revision joint arthroplasty is a technically difficult procedure that often presents intraoperative challenges. For example, difficulties in removing the previous implant or the bone cement may result in an excess removal of healthy bone. Additionally, the bone structure may be damaged from the tools and the length of time required to adequately remove all of the bone cement, may put the patient's safety at risk. A computer implemented system and method for removing bone cement or other material is described in U.S. Pat. No. 5,769,092 assigned to the assignee of the present application. However, there have been advances in imaging which may allow for an improved removal of bone and or bone cement during a revision joint arthroplasty. Thus, there exists a need for a more effective process to adequately remove the previous implant, any bone cement, and prepare a new cavity for a revision implant without further compromising the structure of the bone.

SUMMARY OF THE INVENTION

A process and system for performing orthopaedic surgery with the use of computer systems and robotic assistance to remove bone, bone cement, and a bone prosthesis, typically a bone prosthesis used in hip replacement surgery, knee replacement surgery, and the like. The process for replacing one or more bone prostheses using a robotic system includes receiving image data comprising an image of the bone, the bone including the bone prosthesis implanted within the bone; creating a three-dimensional model of the bone prosthesis and the bone; creating a plan for positioning a new prosthesis within the bone; determining the location and amount of bone material to be removed for the new prostheses; and removing the prosthesis from the bone. Non-bone material such as bone cement is also removed in some embodiments to accommodate a new prosthesis.

The inventive process may be used for the replacement of hip joints, shoulder joints, ankle joints, wrist joints, finger joints, toe joints, or other joints. The inventive orthopaedic surgery can be performed on human; or an animal of a non-human primate, a horse, a cow, a sheep, a goat, a dog, a cat, a rodent, and a bird.

DESCRIPTION OF THE PREFERRED EMBODIMENTS

The present invention has utility as a system and process for performing orthopedic surgery. The following description of various embodiments of the invention is not intended to limit the invention to these specific embodiments, but rather to enable any person skilled in the art to make and use this invention through exemplary aspects thereof. Disclosed herein are systems and processes to use computer systems to remove bone, bone cement, and abone prosthesis, typically a bone prosthesis used in hip replacement surgery, knee replacement surgery, and the like. The removal of bone, bone cement, and/or the prosthesis is performed using robotic assistance. Reference will be made herein to the replacement of hip joints and it should be understood that the present invention may be applied to other joints within the body and any other bones found within the body. These other joints that are repaired through resort to the present invention illustratively include the hip joint, shoulder joint, ankle joint, wrist joint, finger joint, toe joint, or other joint. As used herein, a subject is defined as a human; or an animal of a non-human primate, a horse, a cow, a sheep, a goat, a dog, a cat, a rodent and a bird.

Figure 1:
FIG. 1 is a flowchart depicting a specific embodiment of the present invention for using a computer system for performing revision total joint replacement surgery.
Figure 1:
Figure 1:
Figure 1:
Figure 1:

With reference to FIG. 1, an embodiment of an inventive process is detailed for receiving image data of a subject's bone with a bone prosthesis implanted in block 110; creating three-dimensional (3D) models of the bone prosthesis, the bone cement, and the bone in block 120; planning the location and orientation of a new prosthesis within the bone in block 130; determining the locations and amount of bone and bone cement to be removed in block 140; removing the prosthesis from the bone in block 150; and registering the location of the actual bone during the surgery such that the precise position and orientation of the bone is known by the robot in block 160.

Scan data of a subject's bone and prosthesis as illustrated in block no is readily provided from conventional sources such as computer tomography (CT), magnetic resonsance imaging (MRI), or X-ray scans of subjects' bones, or a combination thereof. The scan parameters in some embodiments are optimized to reduce metal artifact scatter from the prosthesis using a variety of techniques (for example Link, T.; Berning, W; Scherf, S.; Joosten, U.; Joist, A.; Engelke, K. & Daldrup-Link, H. (2000). CT of Metal Implants: Reduction of Artifacts Using an Extended CT Scale Technique. J Comput Assist Tomogr, 24, 1, pp. 165-172, 0363-8715). The scan data may be collected by a system and process described herein or may alternatively, be collected prior to the RTJR surgery.

Development of three-dimensional models of the bone, any bone cement that may have been used in the TJR, and the prosthesis as provided in block 120 may be performed readily using modelling software such as VSG Amira or Medviso Segment to convert imaging scans into models of the bone, bone cement, and the prosthesis of interest. In some embodiments there may be only one prosthesis in each bone, while in others there may be multiple prostheses per bone. The bone, bone cement, and prosthesis will be readily differentiated due to differences in radiodensity or water content.

The preoperative positioning and planning of a virtual three-dimensional model of a new prosthesis or multiple new prostheses relative to the virtual model of the subject's bone is provided at block 130. In certain embodiments of the present invention a model of the subject's bone, bone cement, and prosthesis is created using surgical preoperative planning software. In certain embodiments of the present invention, the preoperative planning software will allow the user to visualize the bone with the original prosthesis and/or the bone cement removed in two or three dimensions. The user will be able to select and position the new prosthesis in three-dimensional space utilizing multiple views. Once the user is satisfied with the fit and placement of the new prosthesis, removal of the old prosthesis may be planned.

The process determines the location and amount of bone and/or bone cement to be removed from the bone based on the 3D model of the new prosthesis is provided at block 140. In some embodiments, the user may manually select the boundaries for the volume of bone and bone cement to be removed, while in other embodiments, the removal of the bone and bone cement may be performed automatically by the computer system. In still other embodiments, the computer may provide the user with an initial estimate of the boundaries for the volumes of bone and bone cement to be removed. In some embodiments, the process may generate a simulation of the model of the bone with the model of the volumes of bone and bone cement to be removed. In still other embodiments, the process may generate a simulation of the volumes of bone and bone cement to be removed with the model of the new prosthesis, and specifically a simulation wherein the model of the new prosthesis is positioned at least partially within the model of the volumes of bone and bone cement to be removed. Additionally, block 140 in still other embodiments also functions to create instructions for a robotic system to mill out the implant shape into the bone to create a cavity that accurately matches the backside of the implant that will be placed into or onto the bone. One such robotic system is the ROBODOC System, manufactured by Curexo Technology Corporation of Fremont, Calif.

The removal of the old prosthesis from the bone is provided at block 150. The method utilized to remove the old prosthesis may depend on a number of factors. In some embodiments of the present invention, the prosthesis is removed from the bone using conventional hand tools including osteotomes, saws, punches, power saws, power burs, and ultrasonic instruments. In still other embodiments, the prosthesis is removed using a robotic system which cuts it out using milling with a rotary bit engaging the prosthesis or through laser ablation.

The registration of the location of the bone intraoperatively within the workspace of the robot is provided at block 160. This serves to determine the precise location and orientation of the bone within the workspace of the robot. In some embodiments, this may be accomplished using fiducial markers placed into or on the bone. A fiducial marker is appreciated to be a material with an opacity that is different than that of surround subject tissue, an active device such as radio frequency identification (RFID) tag, or a combination thereof. In still other inventive embodiments, a registration guide is applied that fits on the bone, or a surface matching algorithm is used, or any other method to determine the orientation of the subject's operative bone. The usage of such techniques are further detailed in: PCT/IB2013/002311 entitled SYSTEM AND METHOD FOR REGISTRATION IN ORTHOPAEDIC APPLICATIONS. S. Cohan, "ROBODOC achieves pinless registration" The Industrial Robot; 2001; 28, 5; pg. 381. P. J. Besl, "A Method for Registration of 3-D Shapes" IEEE Transactions on Pattern Analysis and Machine intelligence, 1992; 14, pgs. 239-256.

Figure 2:
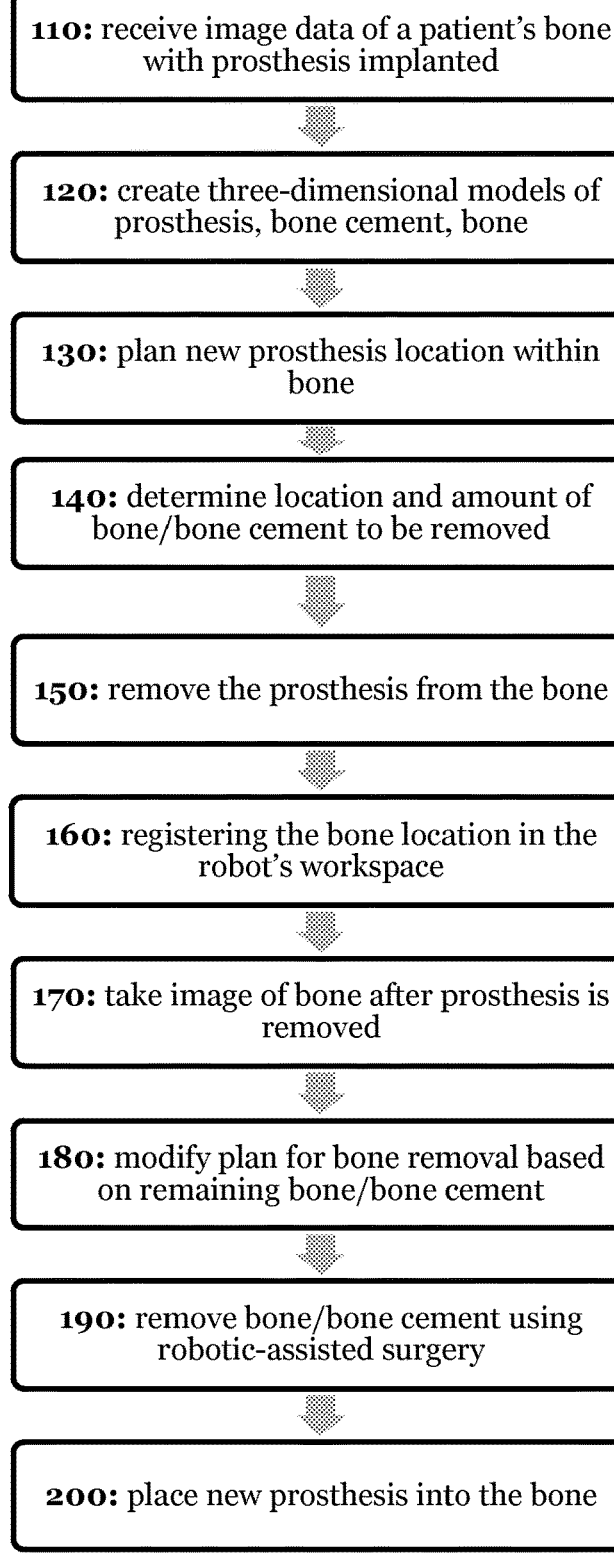
FIG. 2 is a flowchart depicting another specific embodiment of the present invention for using a computer system for performing revision total joint replacement surgery.

As illustrated in FIG. 2, the process illustrated in FIG. 1 may continue by taking images of the bone after the prosthesis has been removed in block 170; modifying the plan for bone removal based on the remaining bone and bone cement in block 180; removing the bone and bone cement using a robotic system in block 190; and placing the new prosthesis into the bone in block 200.

Intraoperative images of the bone after the old prosthesis is removed are taken as provided at block 170. These images may be taken using new techniques for creating 3D volumetric reconstructions such as cone beam CT (CBCT) (Guerrero M E, Jacobs R, Loubele M, et al. State-of-the-art on cone beam CT imaging for preoperative planning of implant placement. *Clinical Oral Investig* 2006; 10:1-7). These images may also be two dimensional as in conventional X-ray images. In some embodiments, these images will be taken prior to removing any and all bone cement in the bone while in other embodiments, these images will be taken after removal of bone cement.

The preoperative plan for removal of bone and bone cement may be modified based on the images taken as provided in block 180. In certain inventive embodiments, the remaining amount of bone cement can be quantified in both volume and location to be removed. In still other embodiments, the process may generate a simulation of the volumes of bone and bone cement to be removed with the model of the new prosthesis, and specifically a simulation wherein the model of the new prosthesis is positioned at least partially within the model of the volumes of bone and bone cement to be removed. Additionally, block 180 in still other embodiments also functions to create instructions for a robotic system to mill out the implant shape into the bone to create a cavity that accurately matches the backside of the implant that will be placed into or onto the bone. In certain embodiments, the user may opt to not take intraoperative images of the bone after the old prosthesis is removed as provided in block 170 and the user may opt not to modify the preoperative plan for removal of bone and bone cement as provided in block 180 and proceed to removal of the bone and bone cement in block 190.

The bone and bone cement are removed using a robotic system as provided at block 190. The robotic system, in one embodiment, mills the planned volumes of bone and bone cement to be removed according to the preoperative or modified plan. In certain inventive embodiments, the milling functions to create a matching cavity to the new prosthesis to be placed within the matching cavity. The newly created cavity in certain embodiments will be the same size or slightly smaller than the new prosthesis such that when the new prosthesis is placed within the cavity, there is direct contact between the bone and the new prosthesis; while in other embodiments a gap is provided to accommodate a bonding agent such as bone cement, mesh, or other interfacial material if so desired.

The new prosthesis is placed into the bone as provided at block 200. In certain embodiments, the new prosthesis may be implanted with or without bone cement to secure the prosthesis to the bone. After the new prosthesis has been implanted, the surgeon finishes the procedure as is done conventionally.

References recited herein are indicative of a level of skill in the art to which the invention pertains. These references are hereby incorporated by reference to the same extent as if each individual reference was explicitly and individually incorporated herein by reference.

As a person skilled in the art will recognize from the previous detailed description and from the figures and claims, modifications and changes can be made to the preferred embodiments of the invention without departing from the scope of this invention defined in the following claims.

What is claimed is:

1. A process for removing a bone prosthesis comprising:
    receiving image data comprising an image of a bone, the bone including the bone prosthesis implanted within the bone;
    creating a three-dimensional model of the bone prosthesis and the bone;
    creating a plan for positioning a new prosthesis within the bone;
    determining a location and an amount of the bone material to be removed for a new prosthesis;
    removing the bone prosthesis from the bone;
    taking an intraoperative image of the bone after the bone prosthesis has been removed to identify remaining bone and any non-bone material;
    modifying the plan for positioning the new prosthesis as to bone removal based on the intraoperative image; and
    removing a portion of the remaining bone, a portion of the non-bone material, or a combination thereof using a robotic system based on the modified plan.

2. The process of claim 1 further comprising registering the location of the bone during a surgery such that a precise position and an orientation of the bone is known to a robot and wherein the removing step is by robotically performing a milling.

3. The process of claim 2 further comprising positioning a set of fiducial markers placed into the bone or on the bone to assist in determining the precise position and orientation of the bone within a workspace of the robot.

4. The process of claim 3 wherein said set of fiducial markers are formed of a material with an opacity that is different than that of bone tissue surrounding one of the set of fiducial markers.

5. The process of claim 3 wherein said set of fiducial markers comprise a radio frequency identification (RFID) tag operating as an active device.

6. The process of claim 2 wherein registering the location of the bone further comprises applying a registration guide on the bone or a surface matching algorithm.

7. The process of claim 1 further comprising removing all of the non-bone material.

8. The process of claim 7 where the non-bone material is bone cement.

9. The process of claim 1 further comprising implanting the new prosthesis into the bone.

10. The process of claim 1 wherein a volume of the amount of the remaining bone to be removed is generated from a model of the new prosthesis.

11. The process of claim 10 further comprising the generation of a volume of the amount of the non-bone material to be removed is generated from a model of the new prosthesis.

12. The process of claim 10 further comprising generating a simulation of the model of the volume when positioning the model of the new prosthesis.

13. The process of claim 1 further comprising generating a simulation of a model of the amount of the remaining bone removed.

14. The process of claim 1 further comprising receiving input from a user to modify boundaries for the amount of the remaining bone.

15. The process of claim 1 wherein the non-bone material is removed.

16. The process of claim 15 where the non-bone material is bone cement.

* * * * *